(12) United States Patent
Cabri et al.

(10) Patent No.: US 9,688,625 B2
(45) Date of Patent: Jun. 27, 2017

(54) AMORPHOUS FORM OF A THIOCOLCHICINE DERIVATIVE

(71) Applicant: Indena S.P.A., Milan (IT)

(72) Inventors: Walter Cabri, Milan (IT); Federico Peterlongo, Milan (IT); Daniele Ciceri, Milan (IT); Andrea Gambini, Milan (IT)

(73) Assignee: INDENA S.P.A., Milano (IT)

( * ) Notice: Subject to any disclaimer, the term of this patent is extended or adjusted under 35 U.S.C. 154(b) by 0 days.

(21) Appl. No.: 15/124,679

(22) PCT Filed: Mar. 26, 2015

(86) PCT No.: PCT/EP2015/056658
§ 371 (c)(1),
(2) Date: Sep. 9, 2016

(87) PCT Pub. No.: WO2015/144857
PCT Pub. Date: Oct. 1, 2015

(65) Prior Publication Data
US 2017/0022155 A1     Jan. 26, 2017

(30) Foreign Application Priority Data
Mar. 27, 2014  (EP) .................................... 14161945

(51) Int. Cl.
*C07C 323/44* (2006.01)
*C07C 319/28* (2006.01)

(52) U.S. Cl.
CPC .......... *C07C 323/44* (2013.01); *C07C 319/28* (2013.01); *C07B 2200/13* (2013.01); *C07C 2103/34* (2013.01)

(58) Field of Classification Search
CPC . C07C 323/44; C07C 319/28; C07C 2103/34; C07B 2200/13
USPC ........................................................ 514/595
See application file for complete search history.

(56) References Cited

U.S. PATENT DOCUMENTS 6,627,774 B2 *  9/2003  Bombardelli ......... C07C 323/41
                                                            564/154

FOREIGN PATENT DOCUMENTS

EP       1263719 A1    12/2002

OTHER PUBLICATIONS

Search and Written Opinion of PCT/EP2015/056658 of Sep. 10, 2015.

* cited by examiner

*Primary Examiner* — Yong Chu
(74) *Attorney, Agent, or Firm* — Silvia Salvadori, P.C.; Silvia Salvadori

(57) ABSTRACT

The present invention refers to an amorphous form of a thiocolchicine derivative, IDN 5404, to a process for producing it and to pharmaceutical compositions thereof. The amorphous form is characterized by the XRPD pattern, DSC profile and/or TG/DTA profile.

6 Claims, 8 Drawing Sheets

AMORPHOUS FORM OF A THIOCOLCHICINE DERIVATIVE

This application is a U.S. national stage of PCT/EP2015/056658 filed on 26 Mar. 2015, which claims priority to and the benefit of European Application No. 14161945.2 filed on 27 Mar. 2014, the contents of which are incorporated herein by reference in their entireties.

The present invention refers to an amorphous form of a thiocolchicine derivative, IDN 5404, a process for its preparation and pharmaceutical compositions thereof.

IDN 5404 having the following formula (I) is a N-deacetylthiocolchicinoid derivative:

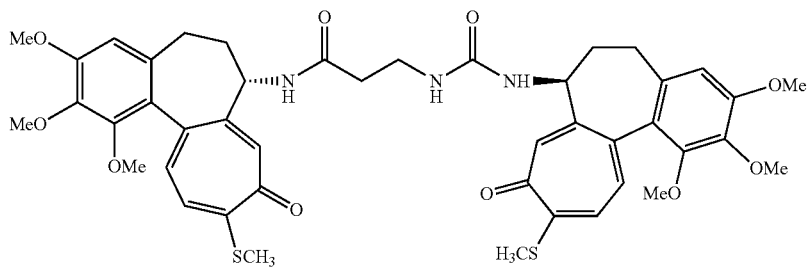

IDN 5404 acts as a vascular disrupting agent, which is a class of compounds able to cause rapid collapse and necrosis of vascular structures. Since endothelial cells of tumours are immature they are much more sensitive to the effects of a vascular disrupting agents than the endothelial cells of normal tissue. IDN 5404 is useful in treating solid tumours, especially if combined with other cytotoxic agents.

IDN 5404 is disclosed in EP 1263719. According to the procedure reported in the example 2 of EP 1263719, the product (Tiocol 54) is first crystallised in EtOAc (as an EtOAc solvate) then is further purified by column chromatography (eluent: Ethyl acetate/hexane or alternatively CH2Cl2/EtOH). The patent does not report the way the product is finally recovered from solution and the form of the final product. Usually the products undergoing purification by column chromatography are recovered simply by evaporating the solvent to dryness. In general amorphous materials are produced by this process. Due to the high insolubility and tendency to co-crystallise with solvents of IDN 5404, upon concentration from the two reported eluting systems, IDN 5404 was obtained either as a EtOAc solvate or EtOH solvate in a crystalline form.

The crystalline form obtained by this process may contain residues of toxic solvents used during the synthetic process, such as dichloromethane and hexane, and it has a very low solubility.

Figure 1:
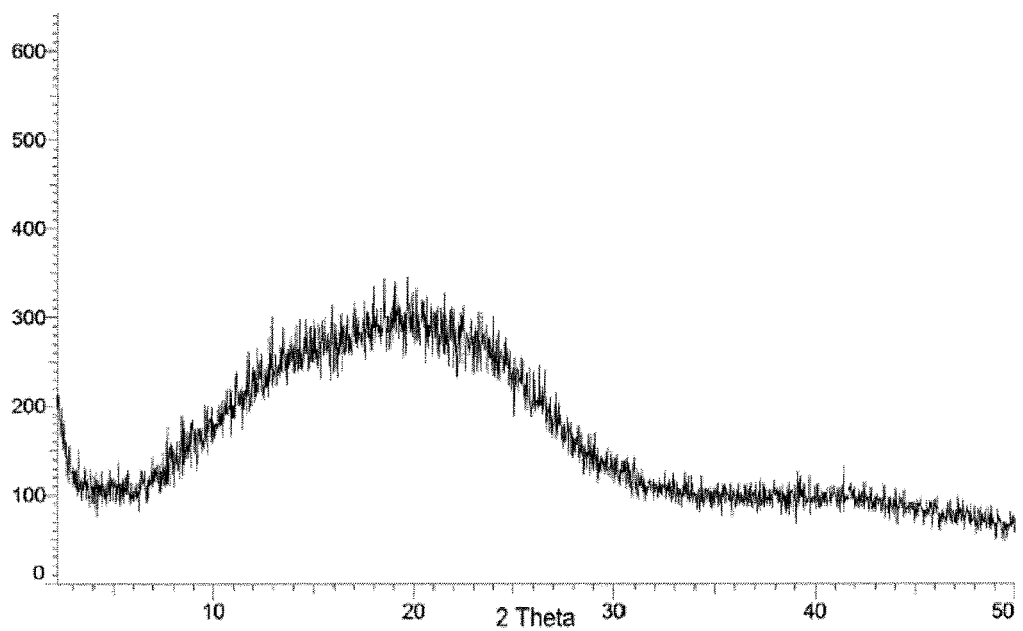
FIG. 1 shows the XRPD pattern of an amorphous compound of formula (I).

Object of the present invention is an amorphous compound of formula (I):

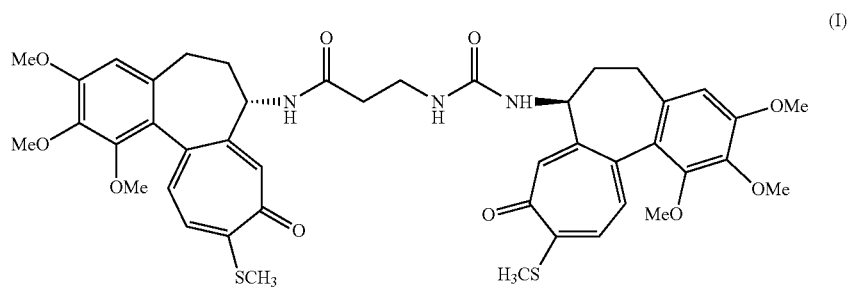

having the XRPD pattern shown in FIG. 1.

The amorphous compound as defined above further characterized by at least one of the following characteristics:
- DSC profile characterized by a glass transition with onset at 186.9° C. and endset at 194.5° C. recorded with a linear heating rate of 10° C./min;
- TG/DTA profile characterized by an endothermic signal between 185.4° C. and 195.4° C. recorded with a linear heating rate of 10° C./min.

The amorphous compound of the present invention may be obtained by a process comprising the steps of:

(a) dissolving the crude compound of formula (I) in DMSO;

(b) removing the possible residual solvents coming from the synthetic process by heating the solution at 65° C. under vacuum;

(c) precipitating the amorphous compound of formula (I) by adding drop wise the solution obtained in step b) to water at 20-25° C. under stirring.

In step a) from 1 L to 8 L of DMSO are preferably used for 1 Kg of IDN 5404.

In step c) from 8 L to 64 L of water are preferably used for 1 Kg of IDN 5404.

The amorphous compound of formula (I) as above defined is more soluble in water than other crystalline forms and it is chemically and physically stable. These properties allow to prepare solid forms containing the compound according to the invention.

Furthermore the compound obtained by the process reported above is devoid of any toxic solvent used during the synthetic process such as dichloromethane and hexane.

The only residual solvent present in the amorphous material is DMSO which is a class 3 solvent (low toxicity).

The above defined amorphous form is not a solvated form differently from the crystalline forms identified by polymorphic screening which are all solvated forms.

The amorphous form of IDN 5404 has advantageous properties in the preparation of pharmaceutical compositions such as such as increased solubility, improved bioavailability, ease of chemical processing and/or ease of pharmaceutical formulation.

Another object of the present invention is therefore a pharmaceutical composition comprising the amorphous compound of formula (I) as above defined and a pharmaceutically acceptable diluent and/or carrier.

The pharmaceutically acceptable diluent or carrier is selected with regard to the intended route of administration and standard pharmaceutical practice. The pharmaceutical formulations of the invention are preferably administered orally or parenterally.

The term "parenteral" as used herein, includes subcutaneous injections, intravenous, intramuscular injection or infusion techniques.

The amorphous form of the present invention may be formulated into conventional dosage forms such as, for example, tablets, pills, suspensions, emulsions, granules, capsules and injection preparations.

The preferred dosage forms for the compounds of the invention are injectable preparations. The compound of formula (I) as above defined may be used, alone or in combination with a cytotoxic agent for the treatment of solid tumors.

EXAMPLE 1

Crude IDN 5404 (1 kg) was dissolved in DMSO (8 L). The solution was heated at 65° C. and kept under vacuum for 2 hours in order to remove completely the solvents coming from the synthetic process. The solution was added drop wise to water (64 L) at 20-25° C. under stirring causing the precipitation of IDN 5404 as an amorphous solid. The resulting material was filtered and dried under vacuum to afford a quantitative yield of IDN 5404.

Characterisation of the Amorphous Form:

X-Ray Powder Diffraction (X-RPD)

X-RPD pattern was recorded on a Bruker D2-Phaser Diffractometer. The x-ray generator was operated at 30 kV and 10 mA, using the CuKα line as the radiation source. The sample was packed on a suitable slit and the irradiated length was 10 mm. Data were collected between 2 and 50 deg 2-theta with a step size of 0.02 deg 2-theta and a counting time per step of 3 sec. The x-ray powder diffraction pattern of Amorphous (FIG. 1) shows absence of diffraction peaks and a broad noise typical of an amorphous sample.

Differential Scanning Calorimetry (DSC)

The analysis was performed using a Mettler DSC1 System. Heat flow was recorded from 30 to 300° C. with linear heating rate (10° C./min) under a 50 ml/min nitrogen flow. About 5 mg of powder was used for the measurement, in closed aluminium crucible (40 µl volume) with a pinhole.

Figure 2:
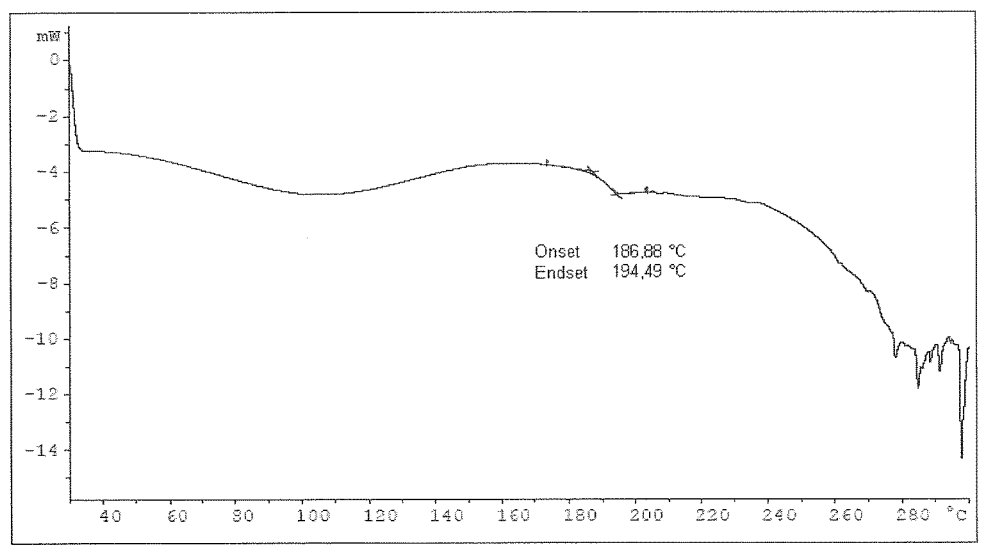
FIG. 2 shows the DSC profile of an amorphous compound of formula (I).

The DSC profile (FIG. 2) is characterized by a broad endothermic signal with maximum at about 100° C. due to release of moisture, and a glass transition with onset at 186.9° C. and endset at 194.5° C.

Fourier-Transform InfraRed Spectroscopy (FTIR)

The infrared spectrum was recorded in Attenuated Total Reflectance (ATR) mode using Fourier-Transform spectrometer Perkin Elmer Spectrum One, equipped with Specac ATR Golden Gate accessory. The spectrum is the result of the acquisition and transformation of 16 co-added scans in the 4000-550 $cm^{-1}$ spectral region at a re.

Figure 3:
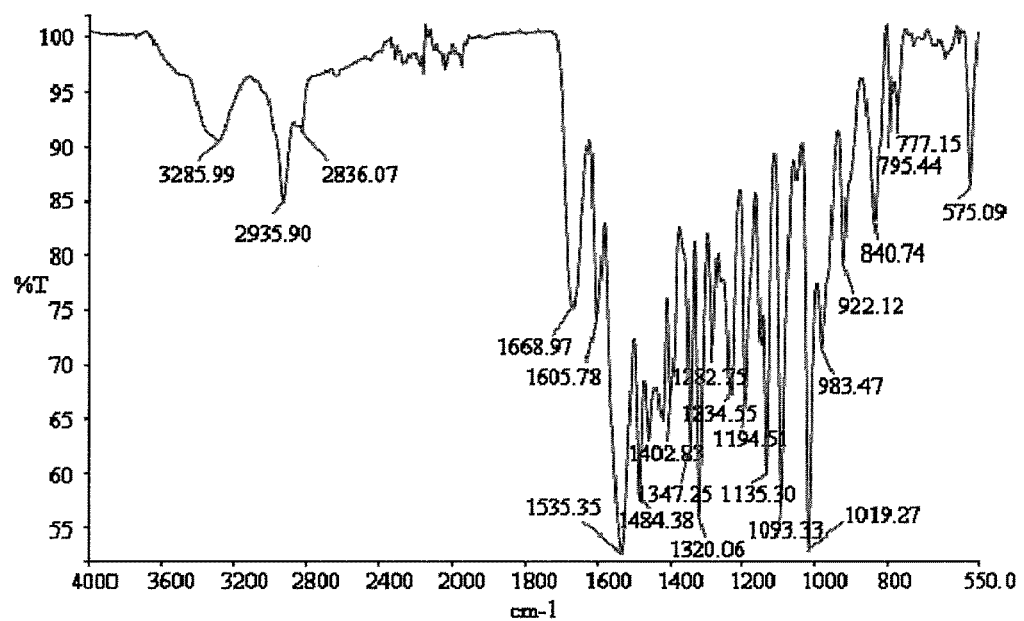
FIG. 3 shows the FTIR-ATR spectrum of an amorphous compound of formula (I).

The FTIR-ATR spectrum is shown in FIG. 3 (the 4000-550 $cm^{-1}$ spectral range). It shows absorption frequencies at 3286, 2936, 2836, 1669, 1606, 1535, 1484, 1403, 1347, 1320, 1283, 1235, 1194, 1135, 1093, 1019, 983, 922, 841, 795, 777, 575 $cm^{-1}$±2 $cm^{-1}$.

Thermogravimetry (TG) and Differential Thermal Analysis (DTA)

The analysis was performed using a Seiko TG/DTA7200 simultaneous system using open aluminum pans (40 µl volume). The TG/DT signals were recorded from 30 to 300° C. with linear heating rate (10° C./min) under a 200 ml/min nitrogen flow. About 10 mg of powder was used for the measurement.

Figure 4:
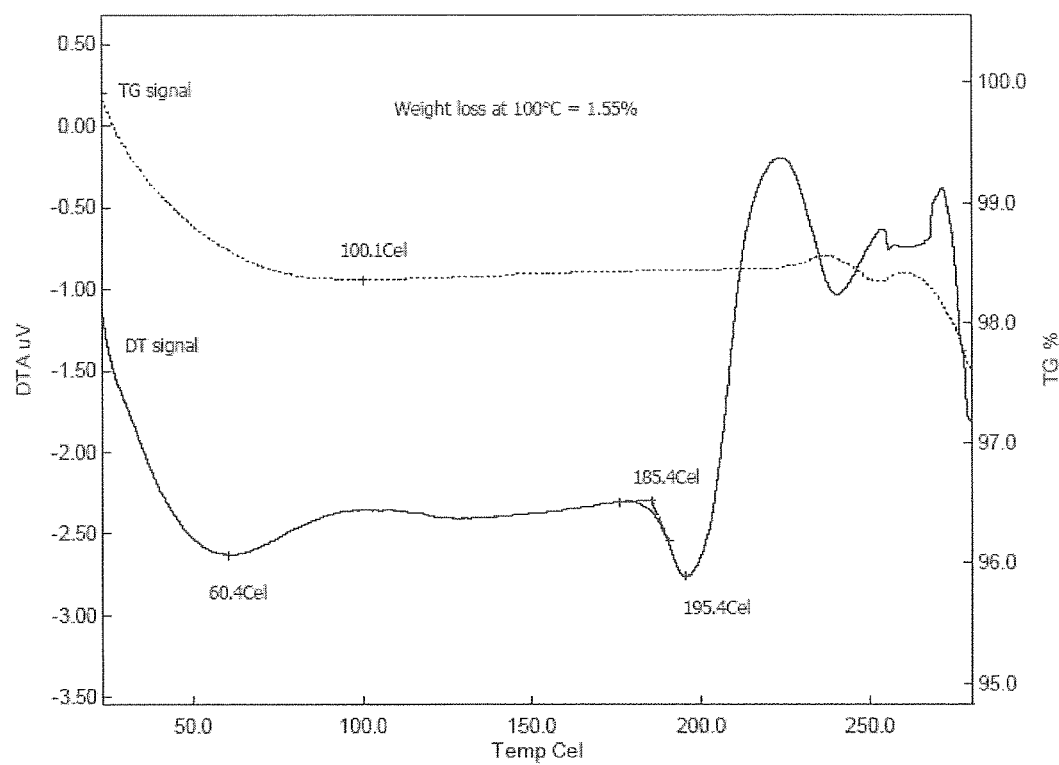
FIG. 4 shows the TG/DTA profile of an amorphous compound of formula (I).

The TG/DTA profile (FIG. 4) is characterized by a broad endotheimic peak with maximum at about 60° C. due to release of residual moisture (weight loss at 100° C.=1.55%), and an endothermic signal between 185.4° C. and 195.4° C. attributable to a glass transition, immediately followed by an exotheimic degradation.

EXAMPLE 2 (COMPARATIVE)

Crude IDN 5404 (500 mg) was purified by flash chromatography using as eluent AcOEt-Hexane 7:3. The fractions containing IDN 5404 were pooled and the solvent removed until dryness. IDN 5404 (310 mg) was obtained as a crystalline yellow solid with the following characteristics.

The product was analysed by GC to determine the residual organic solvents: AcOEt content is 11.1% (22 ppm of hexane) then it was assumed that the product could be a AcOEt solvate.

The TG/DTA and XRPD analysis were performed in the same conditions as example 1.

Figure 5:
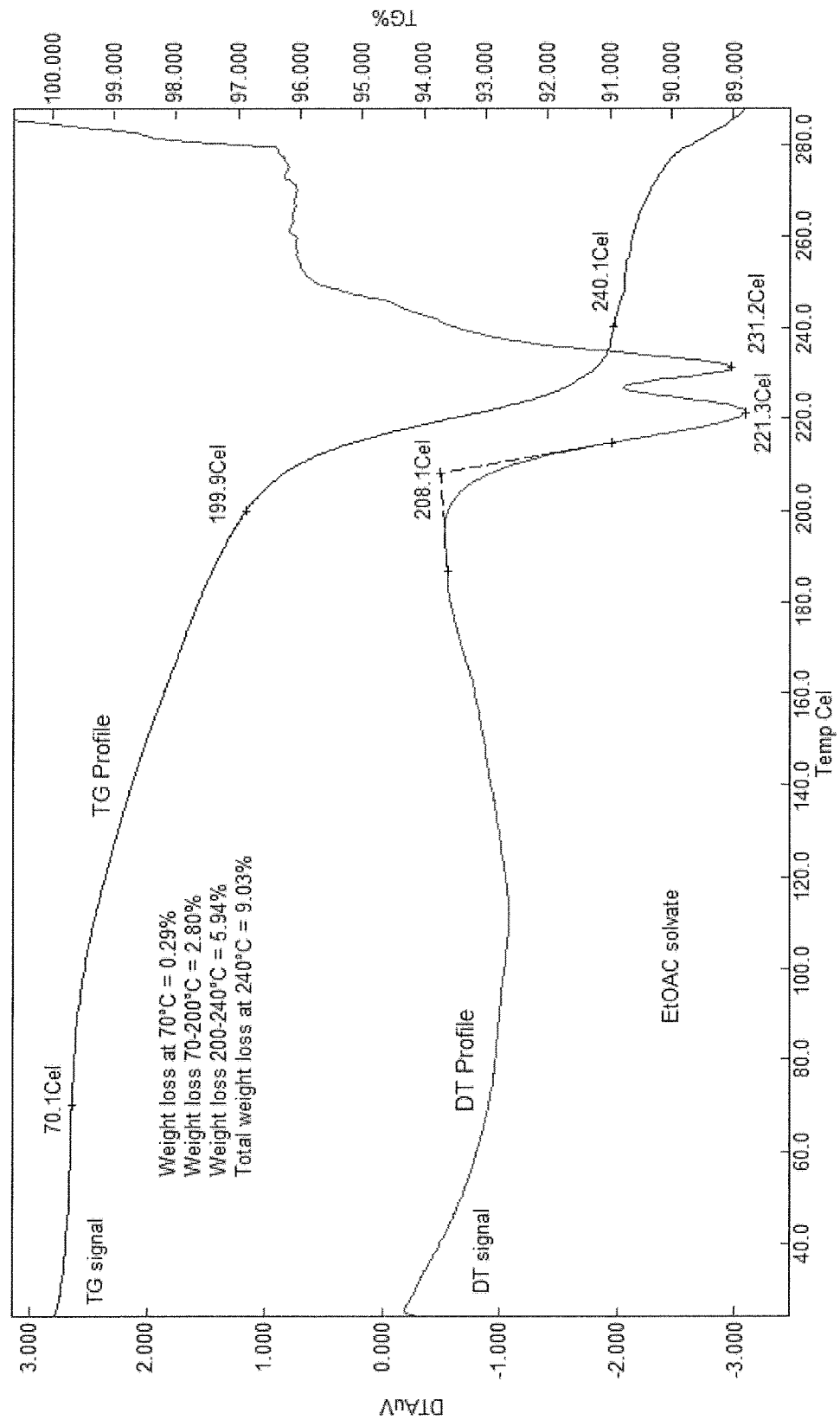
FIG. 5 shows the TG/DTA profile of crystalline product IDN5404 (AcOEt solvate).

The TG/DTA profile of IDN5404 (AcOEt solvate) is represented in FIG. 5. The analysis shows a DT profiles characterized by two intense and not completely resolved endothermic peaks, with onset at about 208° C. and two maxima respectively at 221.3° C. and 231.2° C.

Those peaks, attributable to release of crystallisation solvent followed by melting, are associated to a weight loss of 5.94% from 200° C. to 240° C.

The TG profile shows also a progressive weight loss of about 3.1% from 30 to 200° C., followed by a sharp weight loss in coincidence of the first endothermic peak.

The total loss of weight from 30° C. to 240° C. is 9.0%.

Figure 6:
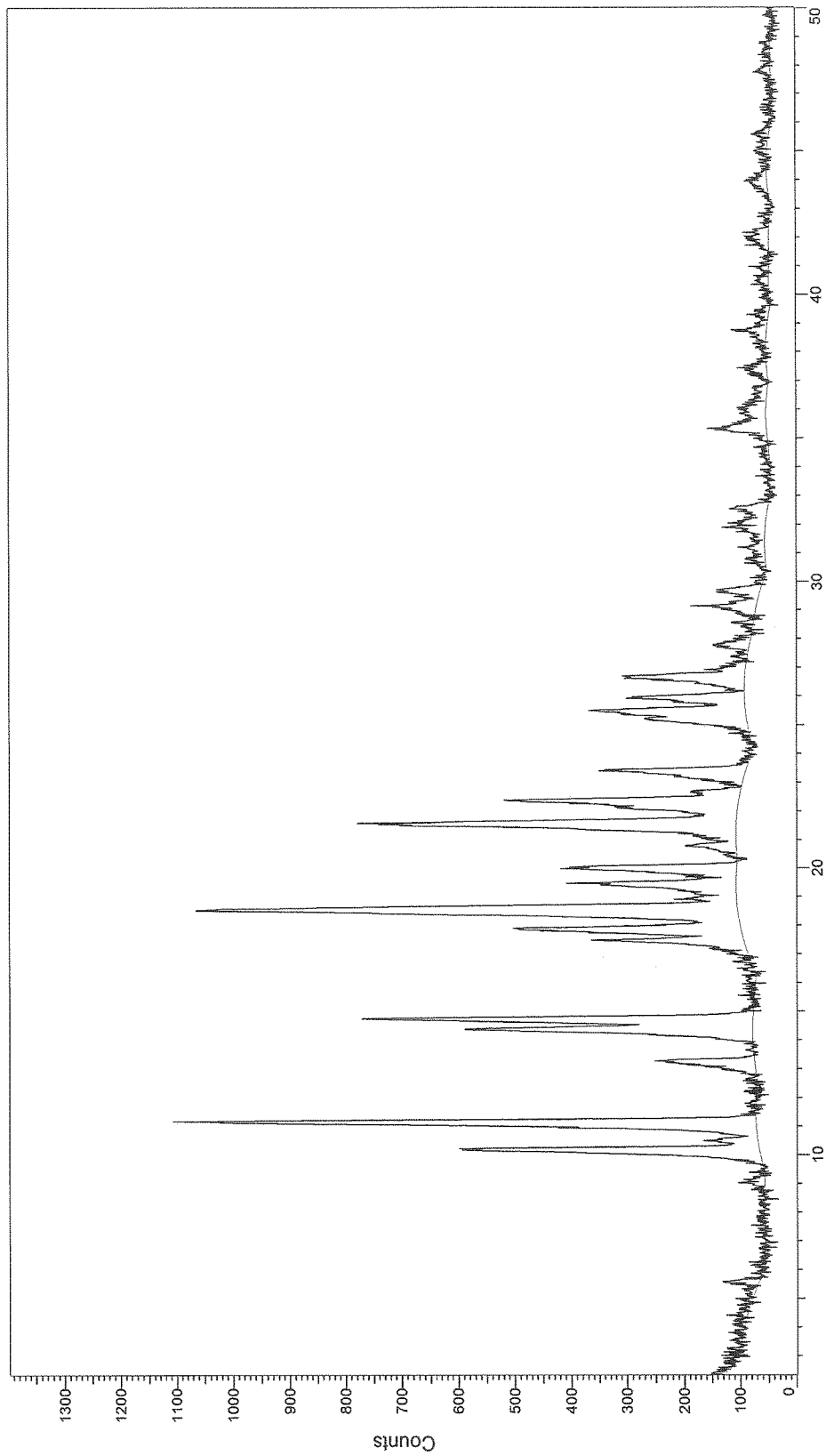
FIG. 6 shows the XRPD diffractogram of crystalline product IDN5404 (AcOEt solvate).

The XRPD diffractogram of IDN5404 (AcOEt solvate) is represented in FIG. 6.

The diffractogram is characterized by intense diffraction peaks and sharp peak profile which indicates high crystallinity; the XRPD pattern shows distinctive reflections, expressed as 2-theta degrees values, at: 5.6-10.2-10.5-11.1-13.3-14.4-14.7-17.5-17.9-18.5-18.9-19.4-20.0-20.8-21.6-22.2-22.4-22.6-23.4-25.2-25.5-25.9-26.7-27.8-28.5-29.1-29.7-30.8-31.2-32.1.

EXAMPLE 3 (COMPARATIVE)

Crude IDN 5404 (500 mg) was purified by flash chromatography using as eluent CH2Cl2-EtOH 95:5. The fractions containing IDN 5404 were pooled and the solvent removed until dryness. IDN 5404 (315 mg) was obtained as a crystalline yellow solid with the following characteristics:

The product was analysed by GC to determine the residual organic solvents: EtOH content is 10.7% (269 ppm of CH2Cl2) then it was assumed that the product could be a EtOH solvate.

The TG/DTA and XRPD analysis were performed in the same conditions as example 1.

Figure 7:
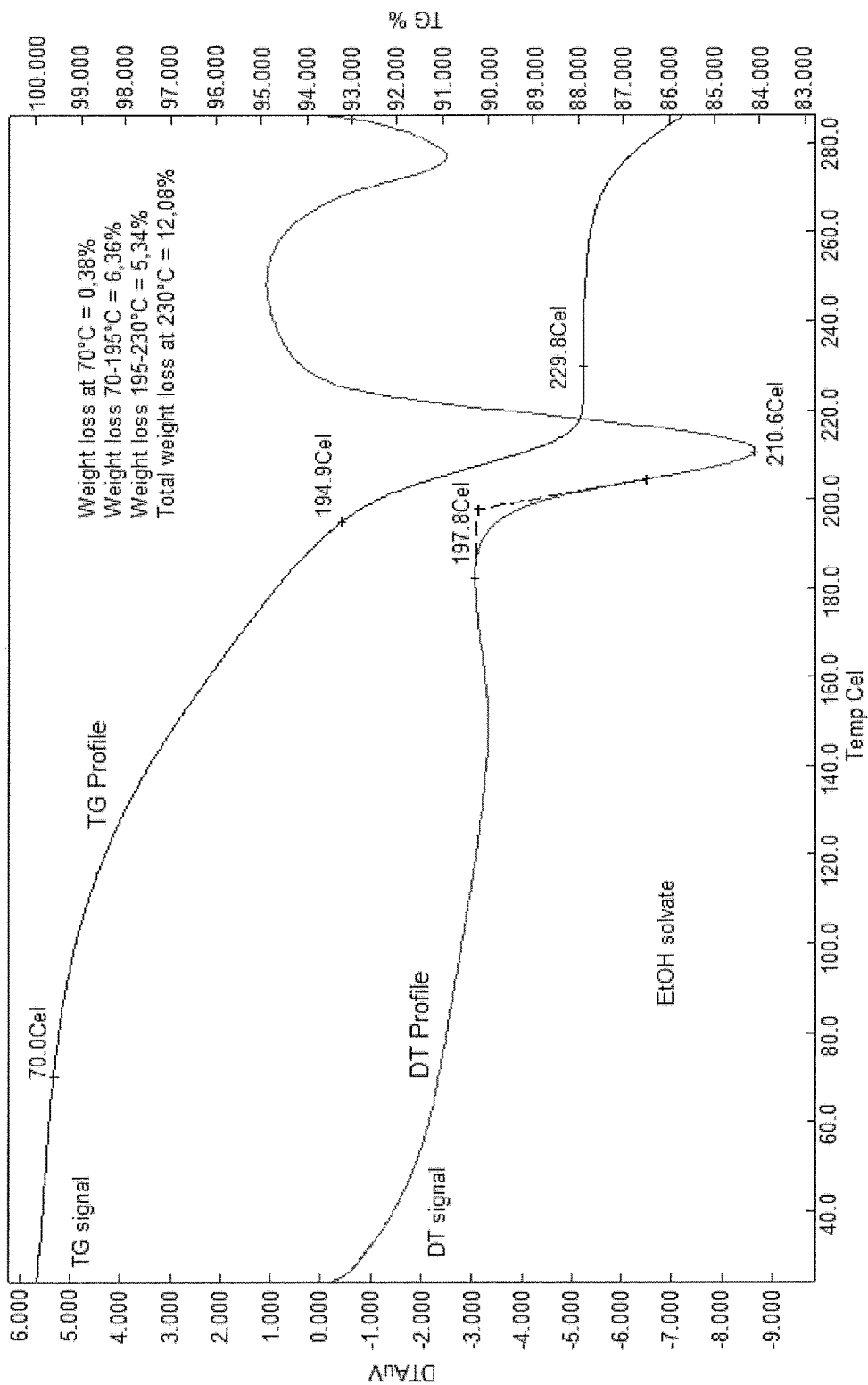
FIG. 7 shows the TG/DTA profile of crystalline product IDN5404 (EtOH solvate).

The TG/DTA profile of IDN5404 (EtOH solvate) is represented in FIG. 7.

The analysis shows a DT profiles characterized by an endothermic peak with onset at about 198° C. and maximum at 210.6° C.

This peak, attributable to melting with release of crystallisation solvent, is associated to a weight loss of 5.34% from 195° C. to 230° C.

The TG profile shows also a progressive weight loss of about 6.7% from 30 to 195° C.

The total loss of weight from 30° C. to 230° C. is 12.1%.

Figure 8:
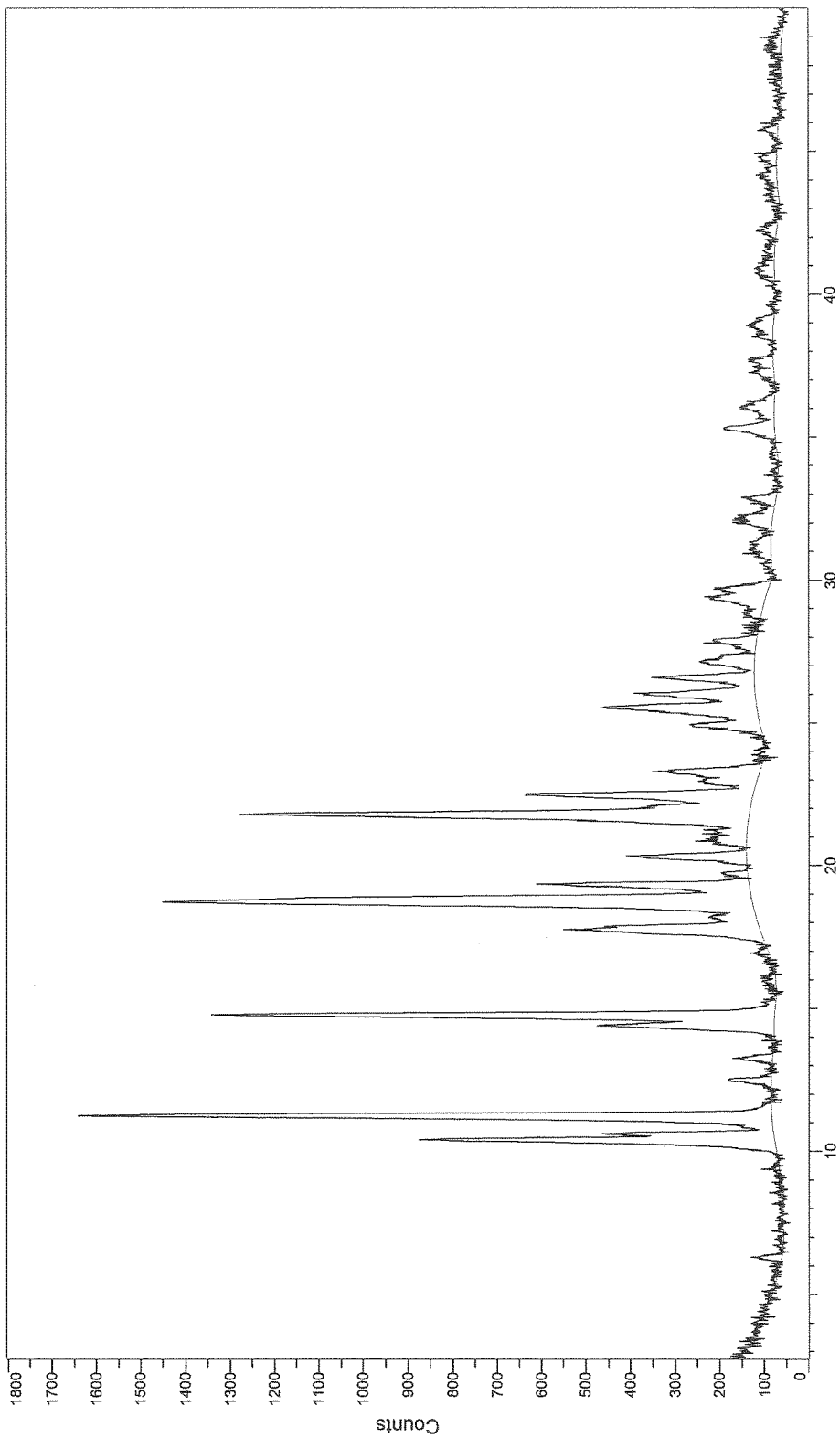
FIG. 8 shows the XRPD diffractogram of crystalline product IDN5404 (EtOH solvate).

The XRPD diffractogram of IDN5404 (EtOH solvate) is represented in FIG. 8.

The diffractogram is characterized by intense diffraction peaks and sharp peak profile which indicates high crystallinity; the XRPD pattern shows distinctive reflections, expressed as 2-theta degrees values, at: 6.3-10.4-10.6-11.2-12.5-13.3-14.4-14.8-16.9-17.8-18.8-19.3-19.7-20.3-20.9-21.8-22.5-23.0-23.3-24.9-25.5-26.0-27.1-27.9-28.9-29.4-29.7-32.2.

Stability Data

The amorphous form of compound (I) has been found to be chemically stable at 25±2° C./60±5% relative humidity for at least three years and at 40±2° C./75±5% relative humidity for at least 6 moths, as none impurity has departed from its initial To value. The analyses were performed by HPLC.

The amorphous form of compound (I) has also been found physically stable at 25±2° C./60±5% relative humidity for at least three years and at 40±2° C./75±5 relative humidity for at least 6 months, as it maintained the characteristics features reported in FIG. 1-4.

The crystalline IDN 5404 obtained in Example 2 shows a variation in the chemical composition of 7% after one month at 40±2° C./75±5% relative humidity.

The crystalline IDN 5404 obtained in Example 3 shows a variation in the chemical composition of 4.1% after one month at 40±2° C./75±5% relative humidity.

The invention claimed is:

1. An amorphous compound of formula (I):

having the XRPD pattern shown in FIG. 1.

2. The amorphous compound according to claim 1 having a DSC profile characterized by a glass transition with onset at 186.9° C. and endset at 194.5° C. recorded with a linear heating rate of 10° C./min.

3. The amorphous compound according to claim 1 having a TG/DTA profile characterized by an endothermic signal between 185.4° C. and 195.4° C. recorded with a linear heating rate of 10° C./min.

4. A process of preparing the amorphous compound of formula (I), as defined in claim 1, comprising the steps of:
  (a) dissolving the crude compound of formula (I) in DMSO;
  (b) removing the possible residual solvents coming from the synthetic process by heating the solution at 65° C. under vacuum;
  (c) precipitating the amorphous compound of formula (I) by adding drop wise the solution obtained in step b) to water at 20-25° C.

5. A pharmaceutical composition comprising the amorphous compound of formula (I) according to claim 1 and a pharmaceutically acceptable carrier and/or diluent.

6. The pharmaceutical composition according to claim 5 for parenteral or oral administration.

* * * * *